United States Patent [19]

Massey et al.

[11] 4,291,421

[45] Sep. 29, 1981

[54] HAND AND FOREARM PROSTHESES

[75] Inventors: Peyton L. Massey, Los Angeles, Calif.; Lester T. Stormon, 1708 Magnolia Ave., Manhattan Beach, Calif. 90266

[73] Assignee: Lester T. Stormon, Manhattan Beach, Calif.

[21] Appl. No.: 80,410

[22] Filed: Oct. 1, 1979

[51] Int. Cl.³ .............................................. A61F 1/06
[52] U.S. Cl. ..................................... 3/12.6; 3/12
[58] Field of Search ............... 3/12.6, 12, 12.7, 12.1, 3/12.2, 12.3, 12.4, 12.5, 12.8

[56] References Cited

U.S. PATENT DOCUMENTS

| 908,881 | 1/1909 | Nelson | 3/12.6 X |
|---|---|---|---|
| 1,271,448 | 7/1918 | Dorrance | 3/12 UX |
| 1,301,367 | 4/1919 | Bowler | 3/12.4 |
| 1,323,671 | 12/1919 | Baehr | 3/12.8 X |
| 1,417,267 | 5/1922 | McElroy | 3/12.4 |
| 1,422,468 | 7/1922 | Nicola | 3/12.7 X |
| 1,423,296 | 7/1922 | Armstrong | 3/12.4 |
| 1,466,163 | 8/1923 | Harris | 3/12.6 X |
| 1,499,052 | 6/1924 | Carson | 3/12 UX |
| 1,725,588 | 8/1929 | Kosek | 3/12.8 |
| 1,929,926 | 10/1933 | Laherty | 3/12.7 |
| 2,347,909 | 5/1944 | Jarrett | 3/12.6 X |
| 2,487,724 | 11/1949 | Pilson | 3/12 |
| 2,540,375 | 2/1951 | Motis | 3/12.4 X |
| 2,542,316 | 2/1951 | Farrar, Jr. | 3/12.6 X |
| 2,556,524 | 6/1951 | Drennon | 3/12.7 |
| 4,156,945 | 6/1979 | May | 3/12.4 |

FOREIGN PATENT DOCUMENTS 522628 4/1929 Fed. Rep. of Germany ............ 3/12

*Primary Examiner*—Clifford D. Crowder
*Attorney, Agent, or Firm*—William H. Maxwell

[57] ABSTRACT

A prosthesis of the hand and including as many finger members thereof as may be required and the forearm as well, and comprised of an articulated thumb and one or more opposed fingers motivated by angular movement of the upper arm relative to the lower arm through pull cords that operate through buffer means to draw said fingers into prehensile grasp with an object and releasable therefrom by a spring bias.

8 Claims, 12 Drawing Figures

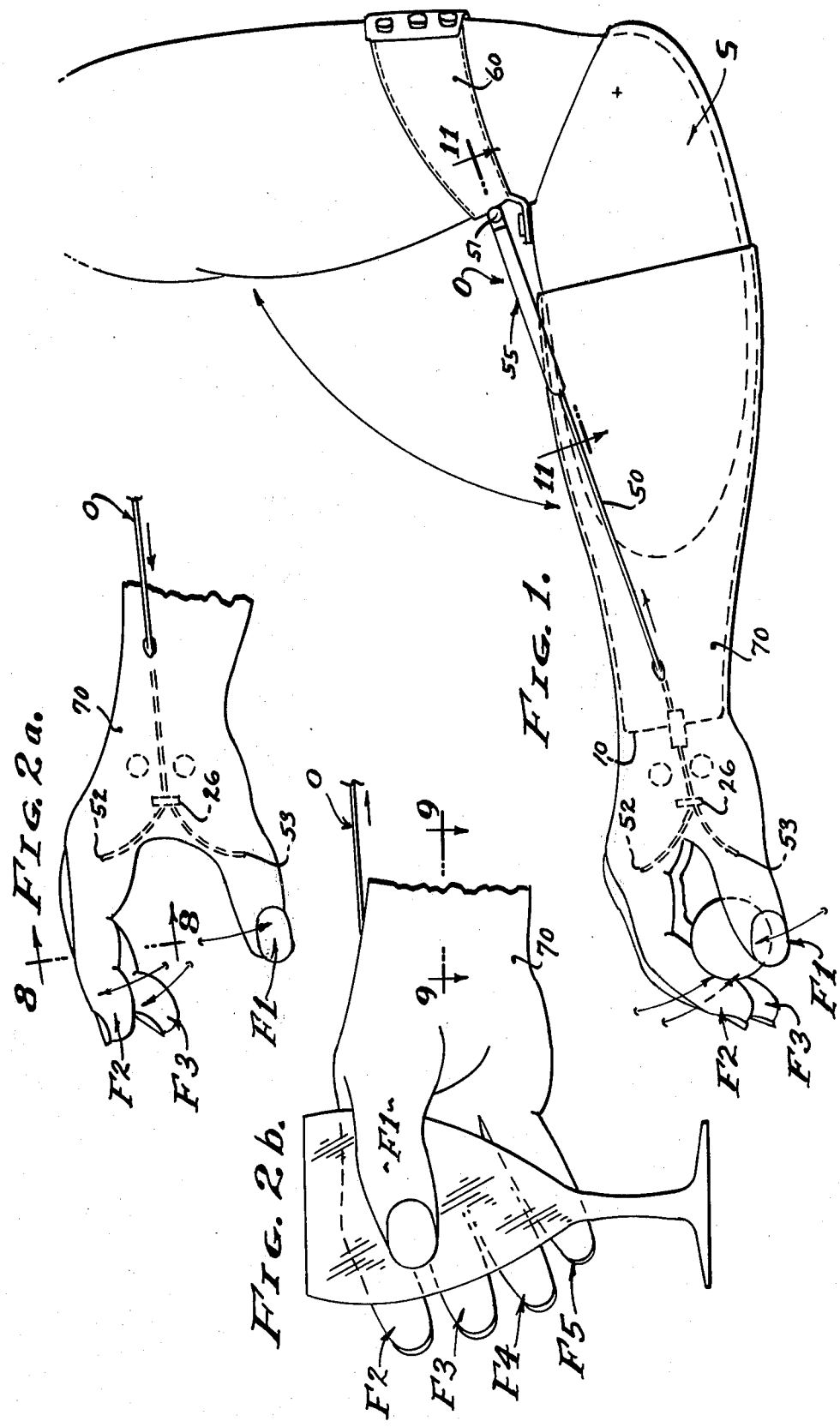

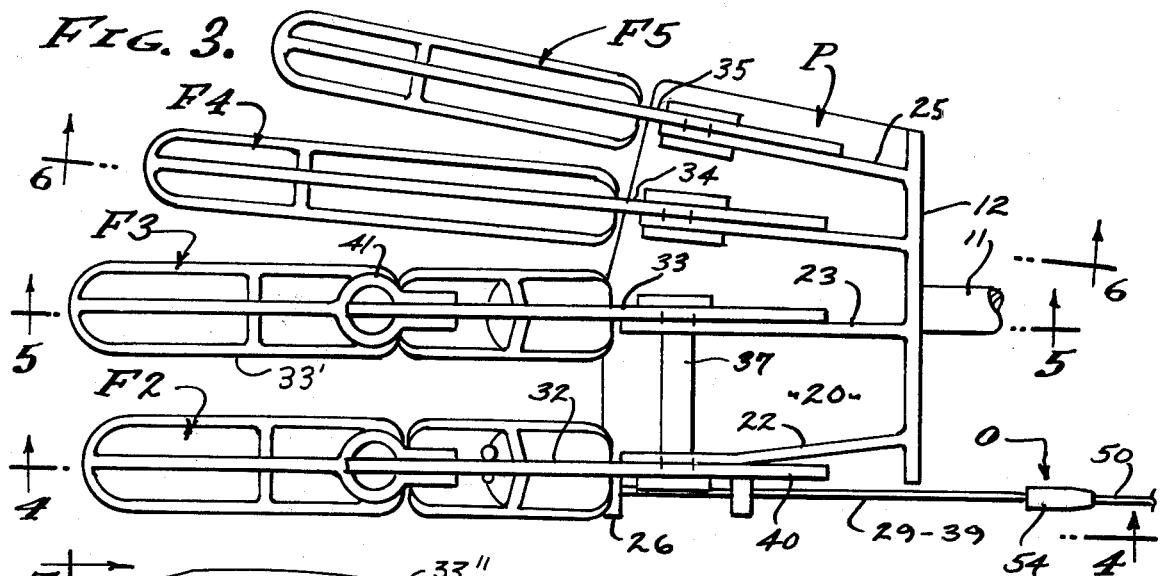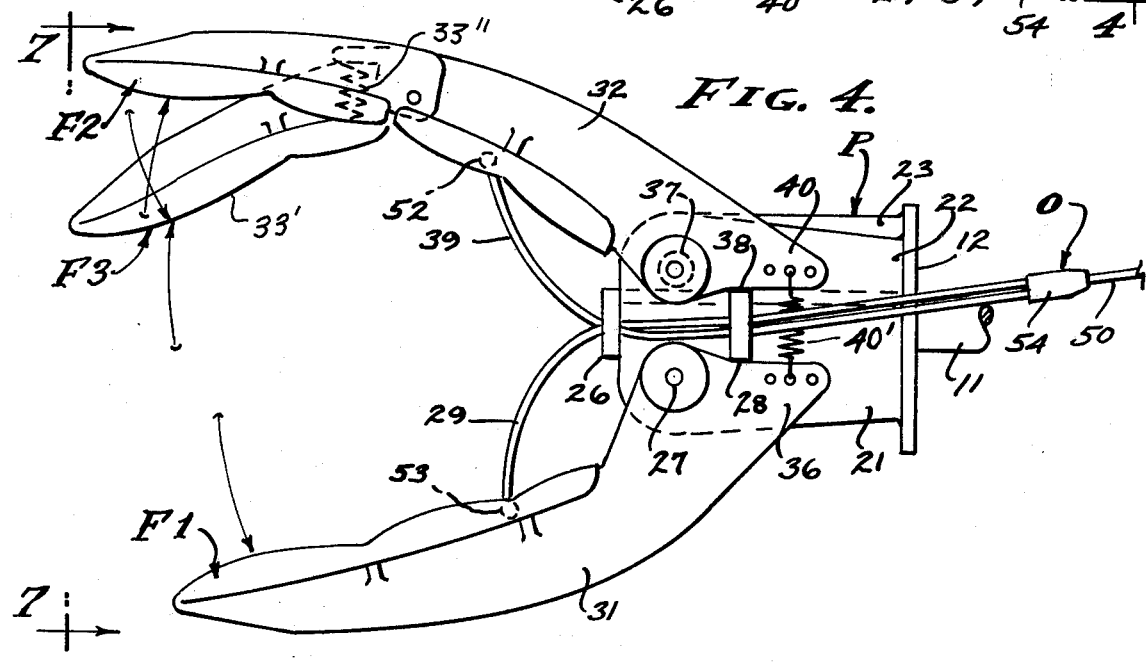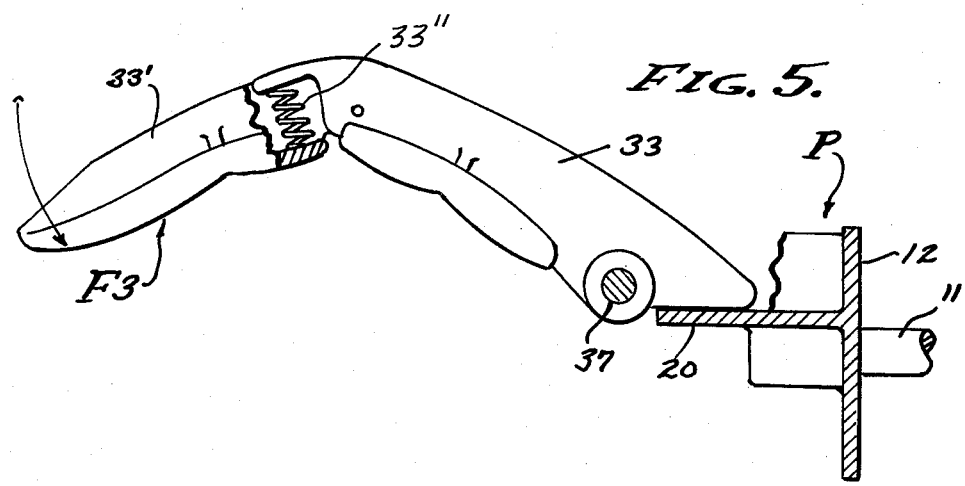

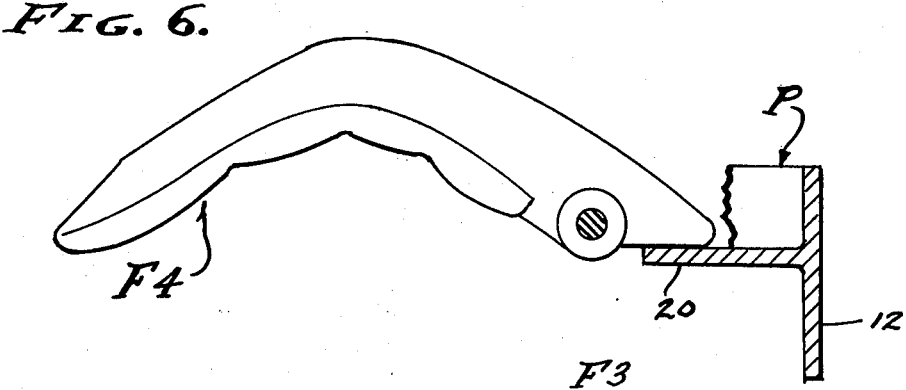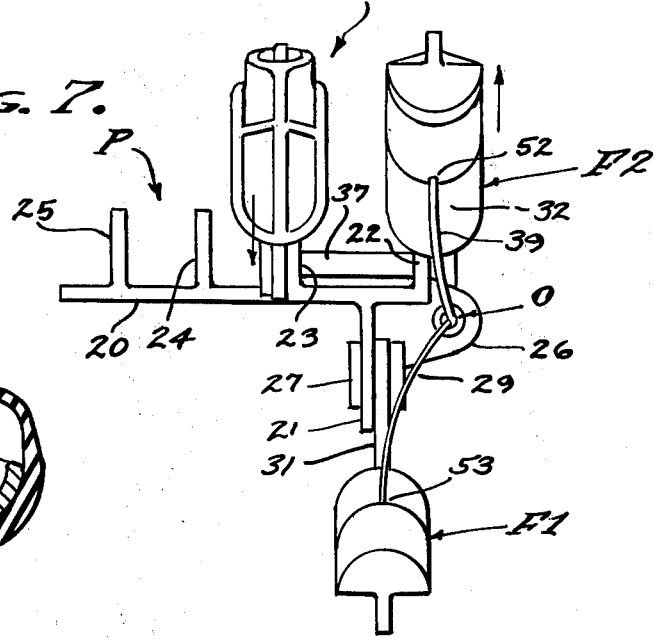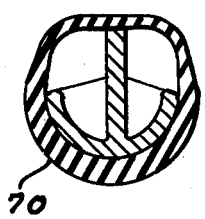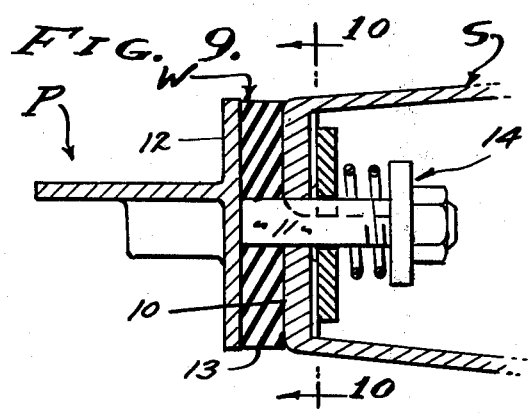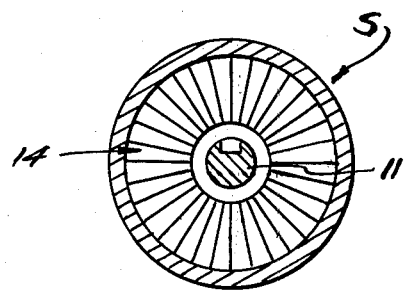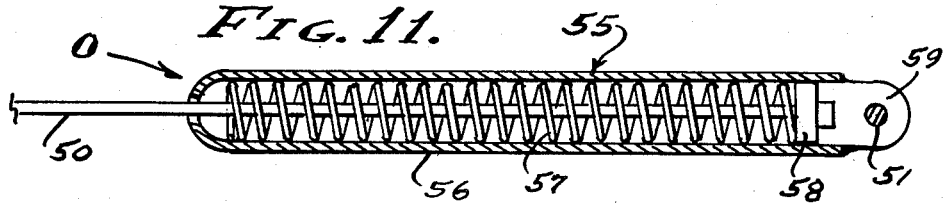

HAND AND FOREARM PROSTHESES

BACKGROUND

The Classic prosthesis for the amputee of a hand or forearm is the "hook", archaic in a sense and in no way comparable to the anatomy of the natural hand; mechanically or cosmetically. It is the prehensile grip and natural appearance that has been lacking in the prior art, and though mechanical arms and hands have been devised, they have been overly complex, excessive in weight and unnatural in both function and appearance. Accordingly, it is a general object of this invention to provide a prosthesis which involves the hand and forearm and provides the natural prehensil function and natural cosmetic value as well.

The human body involves a skeletal frame that supports the flesh, the composite of which involves bone, muscle, fat, and a covering of skin, and the total of which has a certain mass and firmness associated with rigidity. In other words, the parts and limbs of the human body have certain expected physical qualities as well as mechanical functions which enable man to perform. In this case under consideration it is dexterity which is to be reestablished with the amputee, enabling him to perform substantially as before, it being an object herein to provide a prosthesis that operates in a releasible prehensile mode to grip objects the same as a natural hand. With the present invention, all mechanical, there is a thumb that moves in opposition to the index and/or middle finger, to establish a prehensile grip therebetween. Note that there are two or three gripping members. It is also an object of this invention to provide such a prosthesis wherein the mass and firmness is natural, from both the standpoint of feeling and appearance.

The anatomy and movement of body members involves motor means and coupling means to the members to be moved. It is the hand and its moveable finger members with which this invention is primarily concerned, it being an object herein to replace the muscles and tendons that formerly motivated the fingers of the amputee. Accordingly the hand is replaced mechanically as well as cosmetically, and the muscle and tendon complex is replaced by motor means and coupling means operating the mechanical hand in a natural way. In practice, it is the remaining body motions and functions that are employed as the motivating power, under mental control to be governed by the intelligence of the amputee. As will be described, it is assumed that the upper arm and a portion of the lower arm remain intact, in which case it is the relative angular displacement between the humerus and what remains of the radius and ulna that is employed to operate the prehensil movement of the three aforementioned mechanical fingers; the thumb as it is opposed to the index and middle finger.

The prosthesis as it is disclosed herein resembles a forearm and natural hand in every respect, having an extension of the radius and ulna, having carpal and meta-carpal sections, and having each of the proximal, middle and terminal phalanges of the fingers. It is an object of this invention to articulate these mechanical phalanges in a natural manner, so that they are free to move together and so that the thumb is prehensile with respect to the index and middle finger. Principally, it is the proximal phalanges or long bone of the finger that is to be moved as a lever, and with the middle and terminal phalanges carried thereby to be moved therewith. However, a natural feature of this invention is the articulation of one or more phalanges as may be desired; in each case the phalanges having restricted inward and outward movement with respect to the metacarpal section carrying the same. In practice and as shown herein, the middle finger has a spring biased (to close) proximal (middle and terminal) section that straightens when opposed by an object pressured by the thumb. It is to be understood that any one and/or all of the finger joints can be simulated as described herein.

The motor means and coupling means to the mechanical fingers provided as herein above referred to is unique with the present invention, simulating the tendon system of the natural arm and hand. However, the motor and coupling system herein disclosed is simplified and practical, as it employs flexible members anchored to the amputee's upper arm above the capitulum of the humerus and extended to the proximal phalanges to be moved. A feature is the coordinated movement of both the thumb and the opposing index and/or middle finger, whereby the opened prosthesis can be closed upon an object in a natural prehensile manner. Another feature is the positive action of a pull cord system which also includes buffer means that permits over travel of the arm extension of the amputee while increasingly applying prehensile gripping force. Accordingly, the amputee can intelligently apply increased grasping pressures as circumstances require.

It is to be understood that the anatomy to be replaced varies widely according to deformation and injury to a person's body, so that it may be the thumb or any one or more of the fingers that must be replaced, it being an object herein to replace any one of the fingers as herein disclosed. Fundamentally, it is the skeletal frame that is reestablished and all of which is covered by an envelope or glove of plastic material of thickness, softness and suppleness to simulate the skin and finger pads of a real hand. Color, surface texture and imperfections (wrinkles etc.) are included along with fingernails of horn-like plastic; and manicured to match the real hand. Accordingly, realism is achieved with the present invention, for practical as well as for psychological purposes.

A characteristic feature of the human arm and hand appended thereto is the natural ability to revolve the same through approximately 270°. This ability is due to the interaction of the radius and ulna, a function which is effectively destroyed when these two bones are severed. It is an object herein to substitute this rotatability by providing rotation of the prosthesis at the wrist portion between the hand and socket which carries the same. Further, it is an object to avoid unnatural rigid connections of the arm and hand, and with present invention there is flexibility therebetween without adverse effect upon the aforementioned prehensile grip which is so necessary.

The foregoing and other various objects and features of this invention will be apparent and fully understood from the following detailed description of typical preferred form and application thereof, throughout which description reference is made to the accompanying drawings.

DESCRIPTION OF THE DRAWINGS

FIG. 1 is a side view of the prosthesis in a grasping condition on the arm of an amputee.

FIG. 2a is a view of the hand only shown in a relaxed condition, and

FIG. 2b is a view of the hand in a rotated condition grasping an article in the form of a glass.

FIG. 3 is a plan view of the sleletal framework, the outside glove being removed.

FIG. 4 is a side elevation of the framework taken as indicated by line 4—4 on FIG. 3.

FIG. 5 is sectional view of the framework taken as indicated by line 5—5 on FIG. 3.

FIG. 6 is a sectional view of the framework taken as indicated by line 6—6 on FIG. 3.

FIG. 7 is a front elevation taken as indicated by line 7—7 on FIG. 4.

FIG. 8 is an enlarged sectional view taken through one finger by line 8—8 on FIG. 2a.

FIG. 9 is an enlarged sectional view taken through the wrist section as indicated by line 9—9 on FIG. 2b.

FIG. 10 is a sectional view taken as indicated by line 10—10 on FIG. 9.

And FIG. 11 is an enlarged detailed sectional view taken substantially as indicated by line 11—11 on FIG. 1.

PREFERRED EMBODIMENT

The present invention relates to prosthetic devices that replace the missing hand, partially or completely. More particularly, this prosthesis satisfies the needs of malformed and injured person's who do not have complete hands, or no hand at all. It is to be understood at the outset that malformations and injuries vary greatly, and that all or any portion of the prosthesis herein disclosed is to be employed as circumstances require. As shown, the person affected is an amputee who has lost his entire hand and portion of the arm above the styloid processes of the radius and ulna. Consequently it is the entire wrist and hand which is to be replaced and secured to the remaining portion of the radius and ulna. Accordingly, there is a socket S slideably engaged over the severed lower arm, a wrist section W simulating the carpal bones, a palm section P simulating the metacarpal bones, and the articulated fingers extending from the palm section and including one or more of the following; the thumb F1, principally the index finger F2, and the middle finger F3, and the fourth and fifth fingers F4 and F5 when so required. For the purpose of minimizing this discription, the fourth and fifth fingers are shown as fixed in configuration and floating within limits of movement, it being understood that they too can be motivated separately or together the same as the index and middle fingers.

The socket S is an adapter that fits to the amputee's arm, over a secure portion thereof, in this instance over the upper part of the radius and ulna, approaching the inside head of the radius and extending over the coronoid process or elbow. The interior configuration of the socket S conforms to the flesh that surrounds that person's arm portion, and all of which is molded to fit reasonably snug therewith. For example, the socket shown receives and partially embraces the elbow so as to be captured in a working position rotatably oriented with the disposition of the upper arm and humerus thereof. Retainment of the socket and the forearm portion is ensured by the inclusion of the operating means O as hereinafter described, secured to the upper arm and providing a lever system.

The wrist section W replaces the carpal bone that normally pivots on the styloid processes of the radius and ulna, and as shown herein is a rigid portion of the above described socket S. The socket end portion terminates at an end face 10 normal to the axis of the socket that extends to the normal length of the amputee's forearm, having a transverse cross section simulating that of a normal wrist for the particular amputee. In practice, the wrist cross section of face 10 is round, with variations rearward of said face to simulate the styloid process at the outside of the ulna. In other words, the socket S and its wrist section W can be fashioned duplicate the original anatomy of the amputee. A threaded fastener 11 projects axially from the face 10 to mount the hand section P.

The palm section P replaces the metacarpal bones that normally pivot off the carpal bones, and as shown herein is positionably secured to the wrist section W at the face 10 thereof. The palm section is of substantial depth and of a length and plan configuration to duplicate that portion of the amputee's hand. For example, the length of the metacarpals of fingers F2 and F3 are substantially the same, although that of finger F3 may be slightly longer, and while the metacarpals of fingers F4 and F5 are diminishing in length. It is these natural lengths which dictate the palm configuration. In practice, the wrist cross section of the palm section P is elliptical at a plate 12 that is spaced from face 10 by a compressible member 13 of elastomer material through which the fastener 11 extends and rotatably pre-stresses the assembly, as will be described. The compressible member 13 is of rubber or the like and is a geometrical solid truncated to have an elliptical face opposed to plate 12 and a round face opposed to face 10.

The thumb or finger F1 opposes one or both of the fingers F2 and F3, and as shown herein its metacarpal duplication is rigid and disposed laterally of the next adjacent metacarpal of finger F2. It is to be understood that this prosthesis is a simulation of the natural anatomy, and though the metacarpals of the natural thumb F1 and other fingers are at different points hinged, not so with the present invention. Note that the index metacarpal can be rigid in the natural hand. The fingers F1 and F2 herein are both hinged as the metacarpals are considered as essentially rigid. As shown therefore, the thumb F1 is hinged at the bottom side of the palm section P, while the remaining fingers F2-F5 to be opposed by the thumb are hinged at the back side of the palm section P.

The palm section P provides the skeletal frame of the hand and comprises the plate 12 opposed to face 10 of the socket S to which it is rotatably secured by the fastener 11. The transverse median plane that intersects the extended axis of the arm socket S and wrist section W thereof is occupied by a plate 20 having the plan configuration of the palm and back of the hand; that portion comprised of the metacarpal bones. Accordingly, there are upstanding metacarpal ribs 22, 23, 24 and 25 extending forwardly from the plate 20, divergently as are the metacarpals of the natural hand. And, there is a depending carpal rib 21 extending forwardly from the plane 20 beneath the rib 22. The fastener 11 projects from plate 12 to extend loosely through the compression member 13 and through the face 10 and into the socket S where it is coupled to positioning means 14 comprised of incrementally spaced detents biased into pressured engagement so as to be forceably moved into selected positions. As shown, there is an axial interface of circumferentially disposed serrations, one series thereof upon the rearwardly disposed interior of the socket cavity and the other a complementary series thereof upon a forwardly disposed disc or washer keyed to the fastener 11 that revolves with the wrist section W. A spring retained by a nut biases the serrations so that they releaseably secure the hand in whatever rotative position it may be set by the person's other hand.

The ribs 21 and 22 are for mounting the thumb F1 and index finger F2 as will be described, and the depths of these ribs establish the thickness between the palm and back surface of the hand. It will be observed that each rib is to accomodate a finger of the hand, to be fixed and/or articulated as circumstances require. A feature of the palm section P is the inclusion of guide 26 disposed between the thumb and index finger ribs 21 and 22, at the plane of plate 20 and establishing a pull point common to the two said fingers. In practice, said guide 26, and pull point, is located immediately below the plane of plate 20.

The thumb F1 is naturally comprised of the metacarpal, proximal and terminal phalanges, all of which are hinged and muscularly controlled. However, the finger F1 herein is a rigid member wherein the aforementioned bones thereof are integral, said member forming a lever 31 pivotally carried by the rib 21 on a transverse axis. As shown there is a pivot 27 on which the lever 31 is free to rotate from a stop 28 that limits opening motion of finger F1. The lever 31 comprises a flat member engaged with and guided by the side of rib 21, and is a third class lever having a pull member on cord 29 drawing upwardly from a pull point forward of said pivot 27. The back end portion of the lever 31 is extended as a first class lever to form an upwardly disposed leg 36 engageable with stop 28 projecting from the side of rib 21. The finger F1 is of T-shaped cross section, the inside thereof comprising the head of the "T" convexly formed to simulate the pads of a natural finger.

The index finger F2 is naturally comprised of the proximal, middle and terminal phalanges, all of which are hinged and muscularly controlled. The finger F2 herein may be a rigid member, like the thumb F1, wherein the aforementioned bones thereof are integral, said members forming a lever 32 pivotally carried by the rib 22 on a transverse axis substantially parallel to the pivotal axis of finger F1. As shown, there is a pivot 37 on which the lever 32 is free to rotate from a stop 38 that limits opening motions of finger F2. The lever 32 comprises a flat member engaged with and guided by the side of rib 22, and is a third class lever having a pull member or cord 39 drawing downwardly from a pull point forward of said pivot 37. The back portion of the lever 32 is extended as a first class lever to form a downwardly disposed leg 40 engageable with stop 38 projecting from the side of rib 21. The finger F2 is of T-shaped cross section, the inside thereof comprising the head of the "T" convexly formed to simulate the pads of a natural finger.

The stops 28-38 are integrally formed as one part disposed between opposed legs 36 and 40, and between which a tension spring 40' operates to normally engage the legs against said stops and thereby limit opening of the fingers F1 and F2 one from the other. In practice, there is a series of spring points at selectively adjustable radii from the pivots 27 and 37, so that variable opening pressure is obtainable as circumstances require.

The middle finger F3 is naturally comprised of the proximal middle and terminal phalanges, all of which are hinged and muscularly controlled. The finger F3 herein is articulated much the same as the natural finger, in that the middle and terminal phalanges form a rigid member 33' hinged to the proximal phalanges member or lever 33. The member 33' is a biased lever operable between in and out limits, being biased by a spring 33" toward the "in" limit. The lever 33 comprises a flat member engaged with and guided by the side of rib 23, and is a simple lever moveable with the lever 32 of the aforementioned finger F2. As shown, finger F3 is also articulated as is the index finer F2, having a middle and terminal phalange that is biased to an in limit from an out limit.

With the present invention the pivot 37 is a shaft that is keyed to levers 32 and 33, with or without some lost motion therebetween so that the two proximal phalanages can assume individual angular engagement with the object grasped. Thus, the limited motion of finger F2 has general control over the motion of the proximal phalange of finger F3. Note however, the inward depression of the outer phalange lever 33' which assumes a normal inward position simulating the relaxed position of its counterpart in a natural hand. In practice, the lever 33' also comprises a flat member that is bifurcated to embrace the flat member of lever 33 and is thereby guided by limits of rotation extablished by slotted base 41 of the bifurcation engageable with the end of lever 33.

It is the prehensile grip that is reecreated by this invention, wherein the thumb F1 is primarily in moveable opposition to the index finger F2. Also the thumb F1 is in moveable opposition to the middle finger F3, whereby the finger pad at the terminal phalange of finger F1 is moved toward the finger F3, and in practice not in excess of half way between the pads at the terminal phalanges of fingers F2 and F3. For example, finger F1 can remain straight and the pivot 27 tilted in order to direct the terminal pad of the finger as required. As shown, the rib 21 is inwardly offset so that the thumb finger F1 actually operates in opposition to the space that occurs between fingers F2 and F3. Accordingly a three finger prehensile grip is provided, wherein the finger F1 effectively opposes both fingers F2 and F3.

The fingers F4 and F5 are shown as outwardly biased inwardly depressible levers 34 and 35 having in and out limits of rotation pivoted as first class levers to their respective ribs 24 and 25. These two finger members can be free floating or outwardly spring biased as may be required. Each is comprised of T-shaped cross section, the inside thereof comprising the head of the "T" convexly formed to simulate the pads of a natural finger.

In accordance with this invention there is the operating means O which comprises a pull member 50 from an anchor means 51 at the upper arm (humerus), and extending to the pull points 52 of lever 32 through pull member or cord 39 and extending to the pull point 53 of lever 31 through pull member or cord 29. The said pull members or cords 29 and 39 are branches of pull member 50, coupled thereto by a clamp fitting 54 opposite the wrist section W and emmanating through a common cord guide 26. In practice, member 50 is a mono filament Nylon cord of 0.062 inch diameter trained to extend along the inside of the arm and socket S, to emmanate through the guide 26 between the pivots of the two fingers F1 and F2. The mono filament cord is stiff and adapted to be bent and/or warped through gentle curvatures, as shown. A feature therefore is the ferrule configuration of the guide 26 positioned forward of the pivots 27 and 37, and substantially rearward of the pull points 52 and 53. It will be observed that the pull point 52 of finger F2 is approximately the same distance from the pull point ferrule of guide 26 as the pull point 53 of finger F1, thereby controlling the relative angular displacement and the pressure applied. In practice, the pull cord extensions 29 and 39 are also guided through the stops 28–38. It is to be understood that the members 29, 39 and 50 can be straight links, such as straps that are pivotally interconnected.

A feature of this invention is the variable pressure control over the prehensile pincer action of the opposed fingers. To this end the operating means O includes an extensible link 55 in the form of a compressible coupling member having a cylinder 56 in which a compression spring 57 is seated and against which a piston 58 is pulled by the cord 50. As is shown, the open rear end of the cylinder receives the cord 50 which passes through the spring seat end thereof, said open end being flanged to retain a stirrup 59 that attaches to the anchor means 51 in the forearm of an arm band 60. The arm band 60 is of substantial width and surrounds the back of the upper arm above the elbow, where it can also be attached to the rear extremity of the socket S to retain the latter in working position. The anchor point of stirrup 59 is above the pivot point of the natural elbow, a fractional distance of the upper arm length, and accordingly a commensurate mechanical advantage is gained as the forearm is angularly displaced from the upper arm. The spring 57 is of substantial compression, so that the fingers F1 and F2–F3 are moveable without compressing said coupler spring. However, when the relative motion of said fingers is stopped the coupler means 50 provides for over-travel. And, in the event that added prehensile pressure is required, then intelligent angular seperation of the upper and lower arms is applied with comensurate application of increased prehensile pressure.

Referring now to the cosmetic appearance of this prosthesis, the skeletal framework thus far described is covered with a sleeve-like glove 70 of compressible plastic having the color and mechanical properties of a natural hand. In practice molded polyvinylchloride plastic of compressible and pliable supple quality is used. The glove includes all the features and appearance of a hand, including nails, wrinkles etc. Mechanically, it is the prehensile grip of the thumb F1 and opposing fingers F2 and F3 which is to be effective, and accordingly the pad portions of the glove overlying the pads of the above described levers of finger F1 through F5 are of substantial thickness and of a compressibility simulating that of the natural skin replaced thereby. The effect is that the surface of an object being grasped is buried into the glove pad thicknesses to afford frictional engagement of the same as with a natural hand. The skin thickness of the glove skin simulates the real skin and all of which is backed up by the duplicated skeletal members and all to the end that a real hand is closely simulated.

From the forgoing it will be apparent that the skeletal framework and duplication of the anatomy simulates the real and natural bones and their normal articulation. A characteristic feature is the normal open condition of the hand as it is established by relatively light spring pressure. The grasping function is then imposed by tensioning the member 50 and its extensions 29 and 39, utilizing the intelligence of the person wearing this prosthesis. It is an opening angle and extension of the forearm that is employed, and which increases without damage and in face used to advantage to increase the grasping pressure. It is possible therefore, to move the body backward while the arm is extended in order to operate the hand to grasp objects brought into proximity between the prehensile grasp that is established. The structure is made of plastics and non magnetic, and not objectionable to inspections such as those presently conducted in air travel. The structure is light weight and is no heavier than an actual arm, and consequently not tiring and on the contrary is adapted to be readily accustomed to with dexterous results.

Having described only a typical preferred form and application of my invention, I do not wish to be limited or restricted to the specific details herein set forth, but wish to reserve to myself any modifications or variations that may appear to those skilled in the art as set forth within the limits of the following claims:

We claim:

1. A prostheses for replacing the human hand partially and entirely, and including;

a palm section simulating the metacarpal bones, to be secured to the forearm of a person in a disposition duplicating a missing portion of a natural hand, a thumb and at least one other finger simulating the proximal and extending phalanges thereof and pivotally carried in opposition to each other on axes disposed transversely of the palm section, the carpals and metacarpal bones of the thumb and palm section being simulated by ribs extending longitudinally of and projecting downwardly and upwardly from a planar frame member disposed in a transverse medial plane, the metacarpal and phalange bones of the thumb being simulated by a lever member pivotal to a downwardly projecting rib simulating the correspondng carpal bone of the palm section, the phalange bones of the at least one other finger being simulated by a lever member pivoted to an upwardly projecting rib simulating the corresponding metacarpal bone of the palm section, the thumb and at least one other finger being first class levers yieldingly urged against a common stop on the palm section by a spring extending between and operating on the levers at the ends thereof remote from the opposed portions thereof simulating the terminal phalanges, spring means yieldingly urging the thumb and other finger into stopped open positions for the reception of an object to be grasped therebetween, wherein a shaft is rotatable on a said transverse axis and operably connects a multiplicity of said at least one other fingers, the at least one other finger being sectional with its terminal phalange hinged to the distal end of its proximal phalange and yieldingly urged by spring means to an inner limit from an outer restricted limit, and operating means comprised of pull members extending from each of the fingers and through a pull point therebetween and to an anchor point on the uuper arm of the person above the elbow, and wherein said pull members extend to a spring biased coupler that connects to said anchor point for yielding to actuation pressure increasingly applied as angularity between the forearm and upper arm is increased, whereby a forward motion of the person's arm increases the angularity between the forearm and upper arm and draws upon the said members to pull the thumb and other finger together and into engagement with said object to be grasped thereby.

2. The hand prosthesis as set forth in claim 1, wherein a cosmetic glove is slideably installed over said palm section, thumb and at least one other finger and simulating the skin of the hand.

3. The hand prosthesis as set forth in claim 1, wherein a mechanically compressible and cosmetic glove is slideably installed over said palm section, thumb and at least one other finger and simulating the skin of the hand.

4. The hand prosthesis as set forth in claim 1, wherein a mechanically compressible and cosmetic glove of compressible and supple plastic material is slideably installed over said palm section, thumb and at least one other finger and simulating the skin of the hand.

5. A prostheses for replacing the human hand and styloid processes of the radius and ulna, and including,
- a socket member simulating the person's forearm and styloid processes over which it is firmly installed with means securing the same in position as an extension of the remaining inner portion of the forearm,
- a wrist section simulating the carpal bones, and formed as the outer end of the socket member and adapted to receive a section of the hand,
- a palm section simulating the metacarpal bones, secured to the wrist section of the socket member and in a disposition duplicating a natural hand,
- a thumb and opposing fingers simulating the proximal and extending phalanges thereof and pivotally carried on axes disposed transversely of the palm section,
- the carpals and metacarpal bones of the thumb and palm section being simulated by ribs extending longitudinally of and projecting downwardly and upwardly from a planar frame member disposed in a transverse medial plane, the metacarpal and phalange bones of the thumb being simulated by a lever member pivoted to a downwardly projecting rib simulating the corresponding carpal bone of the palm section, the phalange bones of the at least one other finger being simulated by a lever member pivoted to an upwardly projecting rib simulating the corresponding metacarpal bone of the palm section, the thumb and at least one other finger being first class levers yieldingly urged against a common stop on the palm section be a spring extending between and operating on the levers at the ends thereof remote from the opposed portions thereof simulating the terminal phalanges,
- spring means yieldingly urging the thumb and at least one finger into stopped open positions from which they are operable and for the reception of an object to be grasped therebetween,
- wherein a shaft is rotatable on a said transverse axis and operably connects a multiplicity of said at least one other fingers, the at least one other finger being sectional with its terminal phalange hinged to the distal end of its proximal phalange and yieldingly urged by spring means to an inner limit from an outer restricted limit,
- and operating means comprised of pull members extending from the thumb and at least one finger and through a pull point therebetween and to an anchor point on the upper arm of the person above the elbow,
- and wherein said pull members extend to a spring biased coupler that connects to said anchor point for yielding to actuation pressure increasingly applied as angularity between the forearm and upper arm is increased,
- whereby a forward motion of the person's arm increases the angularity between the forearm and upper arm and draws upon the said members to pull the thumb and at least one other finger together and into engagement with said object to be grasped thereby.

6. The arm and hand prosthesis as set forth in claim 5, wherein a cosmetic glove is slideably installed over said palm section, thumb and at least one other finger and simulating the skin of the hand.

7. The arm and hand prosthesis as set forth in claim 5, wherein a mechanically compressible and cosmetic glove is slideably installed over said palm section, thumb and at least one other finger and simulating the skin of the hand.

8. The arm and hand prosthesis as set forth in claim 5, wherein a mechanically compressible and cosmetic glove of compressible and supple plastic material is slideably installed over said palm section, thumb and at least one other finger and simulating the skin of the hand.

* * * * *